United States Patent [19]

Furuoya et al.

[11] 4,092,372
[45] May 30, 1978

[54] CATALYST FOR THE PRODUCTION OF ISOPRENE

[75] Inventors: Itsuo Furuoya, Suita; Atsuo Kobayashi, Nishinomiya; Katsuhiko Ogino, Minoo, all of Japan

[73] Assignee: Takeda Chemical Industries, Ltd., Osaka, Japan

[21] Appl. No.: 674,730

[22] Filed: Apr. 6, 1976

Related U.S. Application Data

[63] Continuation of Ser. No. 564,893, Apr. 3, 1975, abandoned.

[30] Foreign Application Priority Data
Apr. 3, 1974   Japan ................................. 49-38338

[51] Int. Cl.$^2$ ............................................... C07C 1/20
[52] U.S. Cl. .................................................. 260/681
[58] Field of Search .......................................... 260/681

[56] References Cited

U.S. PATENT DOCUMENTS

| 3,207,700 | 9/1965 | Saffer .................................. 252/476 |
| 3,253,051 | 5/1966 | Yanagita et al. ...................... 260/681 |
| 3,662,016 | 5/1972 | Furuoya et al. ...................... 260/681 |
| 3,664,970 | 5/1972 | De Maio ............................... 252/454 |

FOREIGN PATENT DOCUMENTS

39-28632   10/1964   Japan .................................. 260/681

*Primary Examiner*—Delbert E. Gantz
*Assistant Examiner*—J. Thierstein
*Attorney, Agent, or Firm*—Wenderoth, Lind & Ponack

[57] ABSTRACT

A solid catalyst comprising (1) silver ion, (2) aluminum oxide and (3) silicon oxide, which may further comprise, as the fourth ingredient(s), the oxide and/or ion of one or more of transition elements, alkaline earth metals, boron, thallium, tin, lead and phosphorus gives a high yield of isoprene in the reaction of isobutylene and formaldehdye and has a prolonged catalytic activity.

4 Claims, No Drawings

CATALYST FOR THE PRODUCTION OF ISOPRENE

This is a continuation of application Ser. No. 564,893 filed Apr. 3, 1975 now abandoned.

This invention relates to a catalyst for the production of isoprene. More specifically, the invention relates to a catalyst for the production of isoprene by reacting isobutylene with formaldehyde, said catalyst comprising (1) silver ion, (2) aluminum oxide and (3) silicon oxide.

To meet the increasing demand for isoprene as a starting material for the production of synthetic rubbers and the like, it is desired to manufacture isoprene easily in high purity as well as in good yield. For this purpose, the direct production (one stage process) through the condensation between isobutylene and formaldehyde has been recommended on account of its simplified procedures, and there have been reported several catalysts including alumina, silica-alumina, cadmium phosphate, silver oxide, phosphoric acid-chromium oxides (or hydroxides), phosphoric acid-manganese oxides (or hydroxides), silicon oxide-antimony oxide, silicon oxide-bismuth oxide or the like as the catalysts for the one stage process.

However these known catalysts have the following drawbacks:

(1) The conversion of formaldehyde (i.e. the ratio of the amount of reacted formaldehyde relative to that of the supplied formaldehyde) is not necessarily said to be sufficient.

(2) The selectivity of reacted formaldehyde to isoprene is not so high.

(3) As those known catalysts are rapidly degraded by carbon compounds which are inevitably produced in the condensation reaction, the conversion of formaldehyde remarkably decreases with the lapse of the reaction time. So it is necessary to repeat the regeneration procedure of burning the catalysts to remove the said carbon compounds at very short intervals.

(4) The catalytic activity decreases with the repetition of regeneration processes because the heat-resistance of the catalyst is poor and therefore, the life of the catalyst is short.

In consideration of the state of the art, the present inventors have made a search to establish an advantageous process for the industrial production of isoprene through the "one step process". In the course of the search, the present inventors have unexpectedly found that a solid catalyst comprising (1) silver ion, (2) aluminum oxide and (3) silicon oxide, which may further comprise, as the fourth ingredient(s), at least an oxide and/or ion of one or more of the transition elements, alkaline earth metals, boron, thallium, tin, lead and phosphorus, wherein these elements are existing in specific ratio dissolves the above-mentioned disadvantages.

Thus the solid catalyst of the present invention gives isoprene in a high yield as well as high purity and the solid catalyst has a good heat-resistance, and therefore, the life of the catalyst is very long.

The principal object of the present invention is to provide a catalyst industrially usable for the production of isoprene, which is capable of giving isoprene in high purity as well as in high yield with a prolonged life time.

A further object of the present invention is to provide an industrially feasible method for the production of isoprene employing such a catalyst.

The solid catalyst of the present invention can be prepared by combining or mixing a silver component with aluminum component and silicon component and calcining the resulting mixture.

As the silver component, there may be mentioned silver ammine complex ion, silver nitrate, silver acetate, silver cyanide, silver carbonate, silver fluoride, silver chloride, silver sulfate and so on. After all, any silver compound may be employed that can be converted to silver ion by reaction or calcination in the presence of silicon oxide and/or aluminum oxide. Generally, however, silver ammine complex ion is preferred.

The silicon component is exemplified by silicon oxide (e.g., silica xerogel, silica hydrogel, silica sol, crystalline silica or the like); silicic acid salt (e.g. potassium silicate, sodium silicate or the like); silicon halide (e.g. silicon tetrachloride, silicon tetrafluoride or the like); silicic acid ester (e.g. tetraethyl ortho-silicate or the like); other compounds which are easily convertible to silicon dioxide by calcination; clay minerals containing such compounds; or the like. The silicon oxide which is one of the constituents of the present catalyst is preferably lean in alkalis, especially sodium. Thus as sodium ion, the alkali ingredient is preferably not more than 2 weight percent relative to the silicon oxide. When the catalyst is to be manufactured by the ion exchange method, for instance, which is hereinafter described in detail, it is desirable to employ a xerogel of silica. Use of silica hydrogel or silica hydrosol provides for ready mixing with active ingredients, providing a more homogeneous catalyst.

As the aluminum component, use is made of aluminum compounds which can be easily converted to aluminum oxide by calcining or hydrolysis, such as aluminum nitrate, aluminum chloride, polyaluminum chloride, aluminum sulfate, aluminum fluoride, aluminum isopropoxide, aluminum hydroxide, various forms of alumina (e.g. alumina xerogel, alumina hydrogel, alumina hydrosol, crystalline alumina) and so on.

It is also possible to use a compound containing two or more elements to be contained in the contemplated catalyst. There can be exemplified such a compound as silver aluminate, which is a compound of aluminum and silver, or aluminum silicate, which is a compound of aluminum and silicon.

Those three components are combined by admixing or reacting with each other according to the per se known means. For example, there may be employed the method which comprises mixing an aqueous solution or colloidal aqueous solution of said silicon component with an aqueous solution of silver component and an aqueous solution or colloidal aqueous solution of aluminum component and, then, causing the mixture to undergo gelation or precipitation with an alkali or acid; the method wherein water-insoluble members of said components are immersed in water-soluble components or subjected to an exchange with the latter; or the mechano-chemical mixing methods involving the use of a kneader ball mill or other equipment.

This mixing or compounding may be performed in any desired sequence but in case the ion exchange method is employed, for instance, it is preferable to add the silver ion in the last place.

When a silicon component other than silicon oxide is employed or alternatively when an aluminum component other than aluminum oxide is used, it is recommended that the combined materials of the two components are followed by hydrolysis with an aqueous solution of mineral acid (e.g., hydrochloric acid, sulfuric acid or the like) and/or by heating in the presence of oxygen.

The substances other than the constituent members of the catalyst of this invention, for example, nitrate and chlorine ions as well as the alkali, acid or salt thereof used in the gelatin or hydrolysis procedure are all preferably removed by washing with water or other procedures. A heating step is one of the procedures to remove these undesirable impurities by decomposition or sublimation.

In the catalyst according to this invention, the atomic ratio (the ratio of the numbers of atoms) of aluminum to silver is about 1:10 to about 30:1 and preferably about 1:3 to about 20:1. The weight ratio of aluminum oxide to silicon oxide is about 1:5000 to about 2:1 and preferably about 1:1000 to about 1:1.

The thus-obtained components are then calcined at a temperature ranging from about 100° C to about 1,400° C, more advantageously from about 300° C to about 900° C. The calcining procedure is usually carried out in the presence of air, inert gases (e.g. nitrogen, carbon dioxide, etc.), oxygen, hydrogen, water steam or a mixture thereof. The presence of water vapor results in more effective activation and permits use of lower activation temperatures. The calcination time is about 1 to about 24 hours, preferably about 2 to about 10 hours. As the condensation reaction to produce isoprene from isobutylene and formaldehyde is usually carried out at a temperature higher than about 180° C, it is not necessarily essential to effect the calcining procedure prior to use in the reaction.

The thus obtained solid catalyst comprises silver ion, aluminum oxide and silicon component.

In case of using the present solid catalyst in the reaction to produce isoprene from isobutylene and formaldehyde, the following can be considered. The silver ion acts as a soft acid providing an active site for the isobutylene which is a soft base, and the silver ion principally affects the yield of isoprene. The silver ion as such is so thermally unstable that it must be supported on carrier such as silicon oxide. However, in the mixture of silver ion and silicon oxide, the stability of silver ion is still low and the silver ion is readily reduced to silver metal in the course of reaction. Furthermore, the silver ion tends to be converted to oxides such as silver oxide upon drying, heating and so on. As it is, the silver ion becomes extremely stable in the presence of aluminum oxide. Thus, even if such a system is heated to 800° C, for instance, the silver ion does not transform or decompose to silver oxide or silver metal. It has also been found that the silver ion will not be reduced even in the course of reaction.

The solid catalyst of the present invention may further comprise as the fourth ingredient(s), the oxide and/or ion of one or more elements selected from the group consisting of transition elements (e.g. chromium, iron, cobalt, nickel, copper, molybdenum, tungsten, zinc, zirconium, lanthanum, cesium, titanium), alkaline earth metals (e.g. berylium, magnesium, calcium, strontium, barium), boron, thallium, tin, lead and phosphorus. The incorporation of the fourth ingredient or ingredients not only further stabilizes the silver ion but leads to improvements in heat resistance of the catalyst and an extended serviceable life of the catalyst.

The aforementioned fourth ingredient(s) may be incorporated into the contemplated catalyst in various forms, which can be easily converted to ion and/or oxide by heating or hydrolysis, for example as the nitrate, chloride, sulfate, organic acid salt, ammonium salt or the like of the corresponding element(s). The weight ratio of the element(s) of the fourth ingredient(s) to silicon oxide may vary over a broad range, being generally not more than about 20 weight percent or, preferably, not more than 10 weight percent. These fourth ingredients are usually added to the solid catalyst of the present invention before calcination.

By the addition of the fourth ingredient(s) to the catalyst, the yield of isoprene can be increased.

The method for the production of isoprene in which the solid catalyst of the present invention is employed may be effected by the condensation reaction between isobutylene and formaldehyde.

The method per se may be carried out in a similar manner to a known method for catalytic condensation of isobutylene and formaldehyde.

Namely, the molar ratio of isobutylene to formaldehyde may be varied according to the reaction conditions, but an excess of isobutylene, e.g. more than 3 moles of isobutylene per mole of formaldehyde is preferred.

These two starting materials are reacted with each other preferably in vapor phase at a temperature higher than 180° C, preferably from about 200° C to about 400° C in the presence of the catalyst of the present invention.

The reaction may be carried out under atmospheric pressure, a reduced pressure or an elevated pressure, but, rather advantageously, under a slightly elevated pressure, when yield of isoprene is taken into consideration. The usual rate of the reactant gas feed (space velocity) is about 1 mole/hr./$l$.catalyst to about 1000 moles/hr./$l$.catalyst and, preferably, about 10 moles/hr./$l$.catalyst to about 500 moles/hr./$l$.catalyst.

In effecting the method of the present invention, some gaseous materials which do not disturb the reaction may be added to the reaction system as the diluent of the starting materials. The inert gaseous materials are exemplified by water steam, methanol, nitrogen gas, air, carbon dioxide, a paraffin hydrocarbon (e.g. methane, ethane, propane or the like). Particularly, the presence of water steam is desired to prevent the catalyst from an abrupt degradation of activities, and to increase the selectivity of the reacted formaldehyde to isoprene. In this case, the weight ratio of water to formaldehyde is preferably about 1:4 to about 20:1.

Since, in the above-described reaction, the heat of reaction is of a comparatively minor order, no special care is required in temperature control of the catalyst bed. Thus, an adiabatic type reactor serves the purpose well.

When the activities of the solid catalyst have dropped in a long lapse of the reaction time in view of the conversion and selectivity, the catalyst is regenerated by heating the catalyst as about 300° to about 800° C, preferably at about 400° to 700° C in the presence of air, oxygen or water steam, and is applicable again to the condensation reaction.

The shape of the catalyst may be varied to suit the reactor employed.

For example, the catalyst may be made available in a form that may suit any of the fixed bed, fluidized bed, moving bed and transporting-bed type reactors. Thus, for example, by using silica sol as the silicon oxide component and a spray-drying technique, the composition may be easily formed into a catalyst for fluidized bed or transporting bed reactors. A catalyst for moving bed or fixed bed reactors may likewise be easily obtained by using silica sol or silica hydrogel as the silcon oxide component and a wet-molding technique.

When the reaction is conducted in fixed beds, it is preferable to install a plurality of reactors so that the reaction and the catalyst regeneration may be alternately carried out. Or, use can be made of a fluidized-bed, moving-bed or transporting-bed reactor which permits easy circulation of the catalyst and requires only a simple regeneration procedure.

The reaction product is either condensed or absorbed in a suitable solvent, and is recovered by per se known fractional distillation or other conventional procedures. Unreacted isobutylene and formaldehyde can be separated and recycled to the condensation reaction as the starting materials.

Thus isoprene is produced in high convertion ratio as well as in high selectivity, and the obtained isoprene has the supreme purity of more than 99%.

The following examples will serve to further illustrate the method of the present invention with no intention of limiting the scope of the present invention thereto.

In these examples, the conversion ratio as well as the selectivity to isoprene are shown in terms of mean value within the definite reaction time effected. Gram(s), liter(s), milliliter(s) and milliequivalent(s) are simply abbreviated as g., l., ml. and meq. respectively.

EXAMPLE 1

Sodium silicate ($Na_2O.nSiO_2 \cdot xH_2O$; $SiO_2$ 28–30 %, $Na_2O$ 9–10 %) was hydrolyzed with sulfuric acid and, then, washed thoroughly with water to remove the $Na^+$ ions. To 333 g. of thus-obtained silica hydrogel (containing 9.0 wt. % of $SiO_2$ on a dry basis at 110° C) was added 30 ml. of an aqueous solution of aluminum chloride (0.05 mole/l.). While the mixture was kneaded well in an automatic kneader, 30 ml. of an aqueous solution of silver ammine complex ion (0.05 mole/l.) which had been prepared by adding aqueous ammonia to an aqueous solution of silver nitrate. Then, an aqueous solution of ammonium chloride (2 moles/l.) was further added, whereby the gel that had been partially converted to a sol was restored to the original hydrogel state.

This gel was dried at 100° C overnight and the resultant xerogel was crushed and sieved to 10–28 meshes. This xerogel was calcined in a mixture of air and steam at 500° C for 4 hours. The catalyst thus obtained was white in appearance and its X-ray diffraction pattern revealed no evidence of silver oxide.

Ten ml. of the above catalyst was packed into a conventional fixed-bed reactor, and at atmospheric pressure and 300° C, a 40 % aqueous solution of formaldehyde and isobutene were fed at the rates of 3.22 g/hr. and 0.30 mole/hr., respectively. The reaction was carried out for 4 hours.

The reaction product isoprene and the unreacted isobutene were trapped by cooling with dry ice-methanol, while the unreacted formaldehyde and other water-soluble components were absorbed with water. The reaction rate of formaldehyde in the above instance was 90 %, and the selectivity for isoprene was 72 %.

EXAMPLE 2

Granular silica gel (Specific surface area; 380 $m^2$/g.: Average pore diameter; 96A) was crushed to 10–20 meshes and 50 g. of the crushed gel was immersed in 3N aqueous ammonia for 24 hours, whereby the protons on the silica were converted to $NH_4^+$ ions. Then, 100 ml. of silver ammine complex ions (0.05 mole/l.) were added to the gel to exchange $NH_4^+$ for $Ag(NH_3)_2^+$. The silica gel with Ag ions was dried in air and, then, immersed in 170 ml. of aqueous aluminum nitrate (0.03 mole/l.) for 24 hours. Then, the resulting gel was dried at 100° C overnight and calcined in a gaseous mixture of air and steam at 500° C for 8 hours. Like the catalyst of Example 1, this catalyst composition showed no evidence of silver oxide. When the reaction was carried out under the same conditions as with the catalyst of Example 1, the conversion of formaldehyde was 94 % and the selectivity for isoprene was 70 %.

EXAMPLE 3

To 200 ml. of silica hydrosol (Concentration of $SiO_2$; 20–21 weight percent: pH;3-4: Particle diameter; 100–200 A) were added 4 ml. of aluminum nitrate (0.5 mole/l.) and 20 ml. of silver ammine complex ion (0.1 mole/l.), followed by the additon of 2 moles/l. ammonium chloride and 3N aqueous ammonia. The resulting gel was dried at 100° C overnight and comminuted and sieved to a size range of 14 to 32 meshes. The comminuted gel was then calcined in a mixed gaseous current of air and steam at 700° C for 3 hours. Just as in Example 1, there was no evidence of silver oxide that might have been formed. When the reaction was carried out using the above catalyst under the conditions set forth in Example 1, the conversion of formaldehyde was 93 % and the selectivity for isoprene was 69 %.

EXAMPLES 4 TO 7

Catalysts were prepared in the same manner as Example 3. The same reaction was carried out using catalysts with different amounts of $Ag^+$ ion and $Al_2O_3$.

The results are shown in the following table. The result of reaction with an $Al_2O_3$-free catalyst is also shown as a control.

| Example No. | Amount of $Ag^+$ (meg./g. catalyst) | Amount of Al (meg./g. catalyst) | Percent conversion (%) | Percent selectivity % |
| --- | --- | --- | --- | --- |
| 4 | 0.02 | 0.60 | 75 | 73 |
| 5 | 0.10 | 0.45 | 96 | 67 |
| 6 | 0.50 | 2.00 | 97 | 65 |
| 7 | 1.0 | 3.00 | 100 | 60 |
| 3 | 0.05 | 0.15 | 93 | 69 |
| Control (*1) | 0.05 | 0 | 58 | 59 |

(*1) The catalyst had a tinge of brown because of partial formation of silver oxide therein.

EXAMPLES 8–25

To the same silica hydrogel as used in Example 1 were added $Ag^+$ and $Al_2O_3$ in the same manner as Example 1 and, lastly, an aqueous solution of one of the fourth ingredients indicated in the following table was added. The resulting gel was dried and, then, calcined at 700° C for 3 hours. The amounts of so added Cr, Fe, Co, Ni, Cu, Zn, Zr, La, Ce, Mg, Ca, B, Tl, Sn, Pb, P, Mo and W as oxides were invariably 0.0001 mole/g. cat.

The reaction was carried out in the same manner as Example 1. The results are set forth below in the table.

| Example No. | An aqueous solution of the additive Reagent used in preparing the aqueous solution | concentration (mole/l.) | Level of addition (ml./30g.silica) | Percent conversion | Percent selectivity |
|---|---|---|---|---|---|
| 8 | $(NH_4)_2CrO_4$ | 0.05 | 60 | 86 | 78 |
| 9 | $FeCl_3 \cdot 6H_2O$ | 0.1 | 30 | 93 | 63 |
| 10 | $Co(NO_3)_2 \cdot 6H_2O$ | 0.1 | 30 | 92 | 70 |
| 11 | $Ni(NO_3)_2 \cdot 6H_2O$ | 0.1 | 30 | 96 | 64 |
| 12 | $CuCl_2 \cdot 2H_2O$ | 0.1 | 30 | 94 | 61 |
| 13 | $Zn(NO_3)_2 \cdot 6H_2O$ | 0.1 | 30 | 91 | 71 |
| 14 | $ZrO(NO_3)_2 \cdot 2H_2O$ | 0.05 | 60 | 90 | 68 |
| 15 | $La(NO_3)_3 \cdot 6H_2O$ | 0.05 | 60 | 90 | 69 |
| 16 | $Ce(CH_3COO)_3 \cdot H_2O$ | 0.05 | 60 | 87 | 73 |
| 17 | $Mg(NO_3)_2 \cdot 6H_2O$ | 0.1 | 30 | 91 | 69 |
| 18 | $CaCl_2 \cdot 2H_2O$ | 0.1 | 30 | 97 | 67 |
| 19 | $H_3BO_3$ | 0.1 | 30 | 96 | 64 |
| 20 | $TlNO_3$ | 0.025 | 120 | 88 | 71 |
| 21 | $SnCl_2 \cdot 2H_2O$ | 0.05 | 60 | 96 | 61 |
| 22 | $Pb(NO_3)_2$ | 0.05 | 60 | 80 | 78 |
| 23 | $H_3PO_4$ aq. (85 %) | 0.1 | 30 | 62 | 84 |
| 24 | $(NH_4)_6Mo_7O_{24} \cdot 4H_2O$ | 0.05 | 60 | 93 | 69 |
| 25 | $(NH_4)_{10}W_{12}O_{41} \cdot 5H_2O$ | 0.05 | 60 | 91 | 70 |

EXAMPLE 26

To 100 g. of silica sol (Concentration of $SiO_2$; 30 weight percent: pH; 9.6: particle diameter; 130–140A) were added 60 ml. of silver ammine complex ion (0.05 mole/l.) and 40 ml. of aqueous aluminum chloride (0.1 mole/l.), followed by the additon of 30 ml. of aqueous iron chloride (0.1 mole/l.) and 6 ml. of aqueous phosphoric acid (0.5 mole/l.). Then, 3N aqueous ammonia was further added and the resulting gel was wet-molded into granules about 3 mm by 3 mm. After drying at 100° C, the granules were calcined in a current of air at 800° C for 3 hours. When the reaction was carried out with this catalyst under the same conditions as in Example 1, the conversion of formaldehyde was 88 % and the selectivity of the reaction for isoprene was 70 %.

What is claimed is:

1. In a method for producing isoprene through catalytic condensation between isobutylene and formaldehyde, the improvement according to which there is employed as the catalyst a solid catalyst comprising silver ion supported on silicon oxide and stabilized by the presence of aluminum oxide, said catalyst being prepared by mixing (1) a silver ammine complex ion, (2) silcon oxide or a silicon compound which is converted to silicon oxide by calcination, and (3) aluminum oxide or an aluminum compound which is converted to aluminum oxide by calcination, and calcining the resultant mixture, the said catalyst having an atomic ratio of aluminum to silver of about 10:1 to about 1:1, and an atomic ratio of silver to silicon of from 1.215:1000 to 7.13 to 100.

2. A method according to claim 1 wherein the solid catalyst comprises as a further ingredient at least one oxide, ion or mixture thereof of an element selected from the group consisting of transition elements, alkaline earth metals, boron, thallium, tin, lead and phosphorus the weight ratio of elements of the further ingredient to silicon oxide being not more than about 1:5.

3. A method as in claim 1 wherein the atomic ratio of aluminum to silver is about 1:3 to about 20:1 and the weight ratio of aluminum oxide to silicon oxide is about 1:1000 to about 1:1.

4. A method as in claim 2 wherein the ratio of elements of the further ingredient to silicon oxide is not more than about 1:10.

* * * * *